May 10, 1960 J. J. KELLEY Plant Pat. 1,940
FLOWERING QUINCE PLANT
Filed June 30, 1959
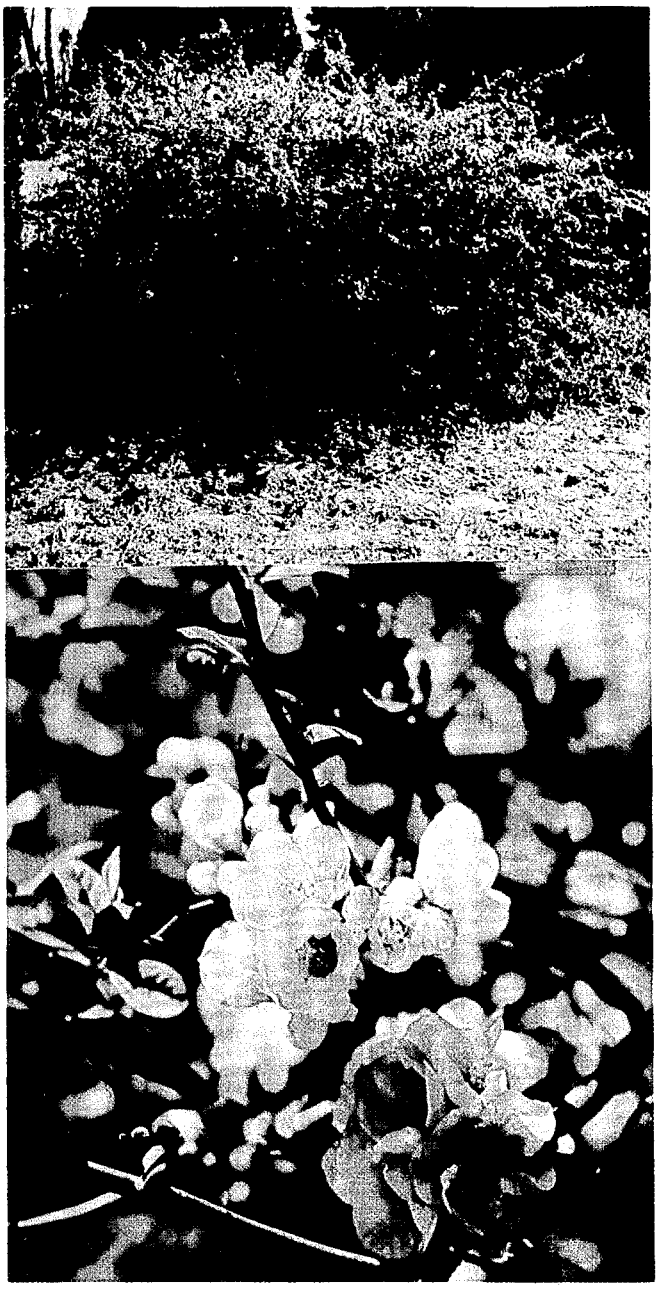
INVENTOR
James J. Kelley
BY Robb & Robb
ATTORNEYS United States Patent Office Plant Pat. 1,940
Patented May 10, 1960

1,940

FLOWERING QUINCE PLANT

James J. Kelley, New Canaan, Conn.

Application June 30, 1959, Serial No. 824,142

1 Claim. (Cl. 47—60)

The present invention relates to a new and distinct variety of flowering quince plant which was discovered by me on cultivated property in my nursery at Darien, Connecticut as a newly found seedling.

At the time of my initial discovery of this seedling, my attention was attracted to a small flowering plant about 12 inches tall and 18 inches in width which was located among evergreens that were being cultivated by me on my nursery property. I was able to identify this small plant as a flowering quince, but the flowers thereof, as well as the habit of growth, appeared to be distinctly different from those of any other variety then known to me. Instead of lightening in color as the flowers mature, according to the usual habit of most flowering quinces, the flowers of the new seedling became darker in color as they developed, beginning with a Pure White color in the opening bud stage, and shading progressively darker to a Deep Rose Pink color as they fully matured. Accordingly, I took steps to mark and carefully preserve the plant, and also to keep it under close observation. Later, I asexually reproduced the same by layering, and also arranged to have other plants propagated by both cuttings and grafting, as performed on my behalf. Continued observations of the original seedling, as well as the asexually reproduced plants, fully confirmed that this flowering quince plant was a new and distinct variety, and is definitely distinguished from all other varieties, as evidenced by the following unique combination of characteristics which are outstanding therein:

(1) A horizontally spreading and twisting habit of growth;

(2) Unusually good foliage retention during the summer months;

(3) Relatively large flowers;

(4) A habit of bearing the flowers in clusters in which the individual flowers open at different times; and (5) An unusual and distinctive flower coloring habit characterized by their Pure White color on opening, then shading slowly and irregularly to Venetian Pink, then through Alizarine Pink and Old Rose, and finally finishing with all the petals being colored a distinctive Eugenia Red color.

Asexual reproduction of my new variety as performed by me by layering at Darien, Connecticut, and also as performed on my behalf by both cuttings and grafting at New Canaan and New London, Connecticut, shows that the aforementioned characteristics and distinctions come true to form and are established and transmitted through succeeding propagations.

The accompanying drawing shows a typical specimen plant, as well as an enlarged view of a typical branch specimen bearing foliage and flowers in different stages of development, all as depicted in color as nearly true as it is reasonably possible to make the same in a color illustration of this character.

The following is a detailed description of the new variety, with color terminology in accordance with Ridgway's Color Standards and Nomenclature, except where general color terms of ordinary dictionary significance are obvious:

(Observations made from specimens grown outdoors at Darien, Connecticut.)

Propagation: Holds its distinguishing characteristics through succeeding propagations by layering, cuttings and grafting.

*Plant*

Growth: Compact; much-branched; dwarf; bush; wider than tall; twisted branch form.

Blooming habit: Heavy; bloom clusters arranged alternately on the branches; buds usually open between April 15 and May 15, with blooms lasting from 2 to 3 weeks; branches may be forced into bloom, but on so doing, colors are not as rich and true as normal, and flowers are not as large.

Foliage:

*Size.*—Small.

*Length (mature).*—Average about 2½ inches.

*Width (mature).*—Average about 1¼ inches.

*Shape.*—Oval; slightly pointed, with serrated edge; 3 or 4 leaves develop from the same bud.

*Quantity.*—Normal.

*Texture.*—Upper side—smooth; glossy. Under side—rough; shiny.

*Veins.*—Prominent.

*Color.*—New foliage (4 days after opening of leaf bud): upper side—Spinach Green, Plate V, Color 29, Tone M; under side—Lettuce Green, Plate V, Color 29, Tone K, with edges Eugenia Red, Plate XIII, Color 1′, Tone—. Old foliage (28 days later than new foliage above): upper side—Hay's Green, Plate XVIII, Color 31′, Tone K; under side—Spinach Green, Plate V, Color 29, Tone M.

Disease and insect resistance: No diseases or insect infestation observed to date under regular growing conditions at Darien, Connecticut.

*Flowers*

Borne: Many to stem; in clusters of 5 or 6 flowers; not all flowers break together, and some vary as much as 7 days apart.

Flower size: From 1¾ inches to 2½ inches in diameter.

Petals: 5 per flower; overlapped.

*Texture.*—Smooth and velvety, both inside and out.

*Shape.*—Disc; from ¾ inch to 1 inch wide.

*Color.*—On first opening, petals are Pure White, then shade slowly and irregularly to Venetian Pink, Plate XIII, Color 1′, Tone F, then through Alizarine Pink, Plate XIII, Color 1′, Tone D and Old Rose, Plate XIII, Color 1′, Tone B, and finally finishing with all petals of the same color Eugenia Red, Plate XIII, Color 1″, Tone —.

*Reproductive Organs*

Sepals: Color (tight-closed bud)—Absinthe Green, Plate XXXI, Color 29″, Tone —, changing to Pale Glass Green, Plate XXXI, Color 29″, Tone F, with tip Old Rose, Plate XIII, Color 1′, Tone B.

Stamens and pollen: Color—Chalcedony Yellow, Plate XVII, Color 25′, Tone —, turning as they develop to Tawny, Plate XV, Color 13′, Tone I, and then as the petals drop to Eugenia Red, Plate XIII, Color 1′, Tone —.

Style and ovary (inferior): Color—Chrysolite Green, Plate XXXI, Color 27″, Tone B.

Stigmas:

*Quantity.*—5.

*Color.*—Deep Seafoam Green, Plate XXXI, Color 27″, Tone F.

I claim:

A new and distinct variety of flowering quince plant, substantially as herein shown and described, characterized particularly as to novelty by the unique combination of a horizontally spreading and twisting habit of growth, unusually good foliage retention during the summer months, relatively large flowers, a habit of bearing the flowers in clusters in which the individual flowers open at different times, and a distinctive flower coloring habit beginning with Pure White color when the flowers first open, then shading slowly and irregularly to Venetian Pink, and then through Alizarine Pink and Old Rose, and finally finishing with all of the flower petals a uniform and distinctive Eugenia Red color.

No references cited.